United States Patent [19]
Banks et al.

[11] Patent Number: 5,919,707
[45] Date of Patent: *Jul. 6, 1999

[54] MONITORING OF ROLLING OIL EMULSIONS

[75] Inventors: Rodney H. Banks, Naperville; Charles C. Payne, Aurora, both of Ill.

[73] Assignee: Nalco Chemical Company, Naperville, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/884,605

[22] Filed: Jun. 27, 1997

Related U.S. Application Data

[63] Continuation-in-part of application No. 08/554,949, Nov. 13, 1995, abandoned, which is a continuation-in-part of application No. 08/361,398, Dec. 22, 1994, abandoned.

[51] Int. Cl.$^6$ ................................................. G01N 21/27
[52] U.S. Cl. .......................... 436/60; 436/164; 73/61.48; 356/70; 356/320
[58] Field of Search .............................. 436/2, 6, 39, 40, 436/56, 60, 164; 356/70, 320, 407, 448, 234; 73/61.48, 61.43, 61.44

[56] References Cited

U.S. PATENT DOCUMENTS

| | | |
|---|---|---|
| 2,852,693 | 9/1958 | Hughes et al. . |
| 3,600,133 | 8/1971 | Price et al. . |
| 3,612,887 | 10/1971 | Canevari et al. . |
| 3,960,740 | 6/1976 | Truett . |
| 4,265,535 | 5/1981 | Pitt . |
| 4,349,353 | 9/1982 | Blumenthal et al. . |
| 4,478,941 | 10/1984 | Hillshafer . |
| 4,548,907 | 10/1985 | Seitz et al. . |
| 4,672,216 | 6/1987 | Pitt et al. . |
| 4,731,332 | 3/1988 | Blumenthal et al. . |
| 4,755,048 | 7/1988 | Kaufman . |
| 4,783,314 | 11/1988 | Hoots et al. . |
| 4,789,483 | 12/1988 | Spei et al. . |
| 4,934,811 | 6/1990 | Watts et al. . |
| 4,976,871 | 12/1990 | Banks . |
| 5,006,311 | 4/1991 | Hoots et al. . |
| 5,068,181 | 11/1991 | Driscoll . |
| 5,077,481 | 12/1991 | Hoult . |
| 5,094,957 | 3/1992 | Willingham . |
| 5,120,661 | 6/1992 | Baker et al. . |
| 5,194,910 | 3/1993 | Kirkpatrick, Jr. et al. . |
| 5,239,180 | 8/1993 | Clarke . |
| 5,282,017 | 1/1994 | Kasindorf et al. . |
| 5,304,493 | 4/1994 | Nowak . |
| 5,332,900 | 7/1994 | Witzke et al. . |
| 5,362,652 | 11/1994 | McClain . |
| 5,389,548 | 2/1995 | Hoots et al. . |

FOREIGN PATENT DOCUMENTS

| | | |
|---|---|---|
| 0 078 544 | 5/1983 | European Pat. Off. . |
| 0 165 061 | 6/1985 | European Pat. Off. . |
| 0 320 086 | 7/1988 | European Pat. Off. . |
| 543057-A1 | 5/1993 | European Pat. Off. . |
| 59-95443 | 6/1984 | Japan . |
| 3-264850 | 11/1991 | Japan . |
| PCT 87/03091 | 5/1987 | WIPO . |
| WO 94/09357 | 4/1994 | WIPO . |

OTHER PUBLICATIONS

K. R. Januszkiewicz, Lubrication Engineering, 1992, vol. 48, 56–61.

K. R. Janusziewicz, Lubrication Engineering, 1991, vol. 47, 448–452.

*Primary Examiner*—Jeffrey Snay
*Attorney, Agent, or Firm*—Margaret M. Brumm; Thomas M. Breininger

[57] ABSTRACT

The concentration of the active ingredient in a rolling oil emulsion can be rapidly determined, and correction of the concentration of the active ingredient can be undertaken by measuring the measuring the amount of light reflected from the emulsion at the peak absorbing wavelength of the dye to obtain a first reflectance value and measuring the amount of light reflected from said emulsion at a wavelength other than the peak absorbing wavelength of the dye to obtain a second reflectance value for at least two different concentrations of the rolling oil in the rolling oil emulsion, establishing a calibration curve, and then monitoring the rolling oil emulsion in like manner. The results may be utilized to feed additional additive to the emulsion, or may be used to feed water into the emulsion system.

9 Claims, 1 Drawing Sheet

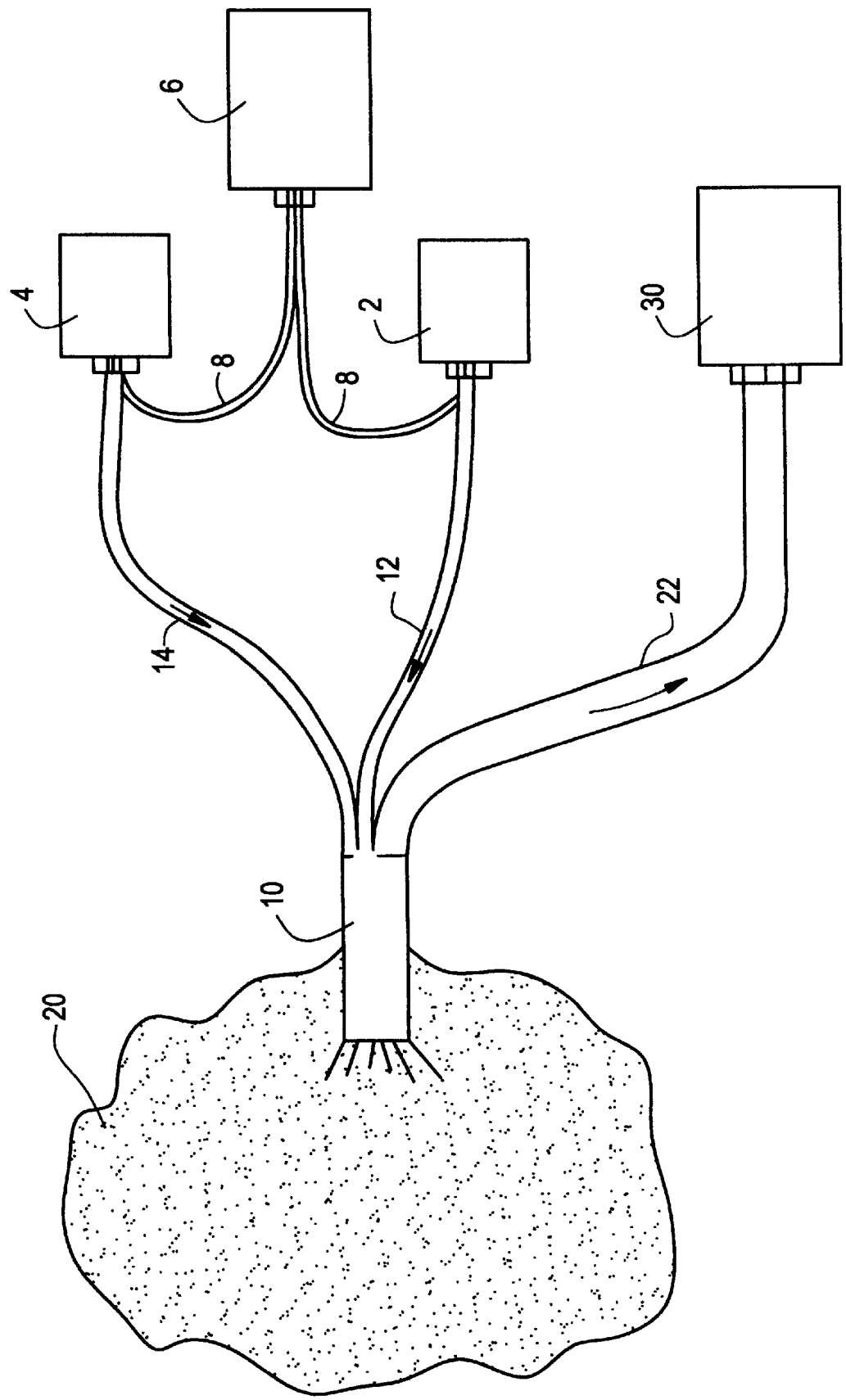

5,919,707

MONITORING OF ROLLING OIL EMULSIONS

This application is a continuation-in-part of Ser. No. 08/554,949 which is in turn a continuation-in-part of Ser. No. 08/361,398 filed Dec. 22, 1994, now abandoned, hereby incorporated by reference.

FIELD OF THE INVENTION

This application relates to a method for determining the concentration of a rolling oil in an aqueous emulsion used in the rolling or shaping of metals. The method involves adding a dye which has a peak absorbance in the visible or near infra-red region to the rolling oil composition, forming an emulsion from the composition, providing a source of light at two wavelengths, one at the absorbing wavelength and the other at a nonabsorbing wavelength to the dye, and ratioing the intensities of the reflected wavelengths from the emulsion. This method is particularly useful in determining rolling oil levels in emulsions contaminated with other organic materials which may interfere with traditional methods involving UV absorbance, fluorescence, or volume measurements following emulsion breakout.

BACKGROUND OF THE INVENTION

An optical apparatus and method for the determination of impurity components present in both homogeneous and non-homogeneous light-scattering products with light sources having wavelengths in the visible and near-infrared regions has been disclosed in U.S. Pat. No. 4,755,048. The objective of that method is to measure the impurity level and product level in a light scattering material, with a requirement for the monitoring of three wavelengths for background, impurity and product. For the operation of Kaufman's apparatus and method, it is necessary to first characterize the component to be monitored such that a readily monitorable characteristic peak may be identified.

By contrast, this invention is a simpler technique, in which a product level is inferred by measuring only the concentration of a proportionally-added marker by the ratioing of two scattered wavelengths (one corresponding to the marker and one corresponding to the matrix). Even if the product has no readily monitorable peak, this invention will work. Moreover, for this invention, there is no requirement to determine a wavelength which is absorbed by components to be monitored, but rather only a minimal requirement to determine where the components to be monitored do not absorb.

Although Kaufman suggests the use of an optical marker when the product has no readily distinguishable absorption band, his method still involves a comparison at three wavelengths, that of the impurity, that of the product (as enhanced by the optical marker), and that of the background. The impurity is still directly monitored by this method. Thus, as will be described, this invention is more efficient than that disclosed by the Kaufman reference because there is no requirement that a product be directly monitored, nor is there a need to monitor three different wavelengths in order for the method to operate.

SUMMARY OF THE INVENTION

The present invention allows for the accurate control of process additives, and especially consumable process additives in rolling oil systems by the introduction into the system of a substantially inert dye which will absorb light at a given maximum or peak wavelength. This dye is added in direct proportion to the amount of rolling oil additive that is desired to be monitored, and the concentration of the additive or oil is monitored by measuring a reflectance value at the peak absorbing wavelength of the dye, ratioing this reflectance value with a reflectance value taken at a wavelength at which the dye does not absorb. The system described herein allows accurate process measurements to be taken of rolling oils that can be substantially opaque.

It is an object of this invention to provide to the art a method for determining the concentration of a rolling oil composition in an emulsion using optical reflectance measurements. It is a further object of this invention to allow the monitoring and control of the concentration of a component in a rolling oil emulsion using reflectance measurements. It is a still further object of this invention to provide to the art a method for controlling the concentration of a component of a rolling oil emulsion using optical reflectance measurements. Further objects will appear hereinafter.

BRIEF DESCRIPTION OF THE DRAWING

FIG. 1 is a schematic drawing of a measuring device capable of being used in the practice of the subject invention. FIG. 1 will be more fully described herein.

THE INVENTION

The basic process of this invention encompasses a method for determining the concentration of a rolling oil composition or product in a working rolling oil emulsion. The method generally comprises the steps of:

I. Preparing a calibration curve through the steps of:

a. Adding a known concentration of a dye to the active ingredient of a rolling oil emulsion;

b. Applying a light source to at least a portion of the rolling oil emulsion containing the active ingredient;

c. Measuring the amount of light reflected from said emulsion at the peak absorbing wavelength of the dye to obtain a first reflectance value and measuring the amount of light reflected from said emulsion at a wavelength other than the peak absorbing wavelength of the dye to obtain second reflectance value for at least two different concentrations of the active ingredient in the rolling oil emulsion;

d. Ratioing the second reflectance value with the first reflectance value for each concentration of active ingredient to establish a concentration calibration curve; and then, II. Determining the concentration of active ingredient in a rolling oil during use through the following steps:

a. Obtaining a sample of emulsion after the emulsion has been in use;

b. Measuring the amount of light reflected from said emulsion sample at the peak absorbing wavelength of the dye to obtain a first reflectance value and measuring the amount of light reflected from said emulsion at a wavelength other than the peak absorbing wavelength to obtain a second reflectance value;

c. Ratioing the second reflectance value with the first reflectance value and comparing the value obtained with the calibration curve of step I(d); and then, d. Determining the concentration of the active ingredient in the rolling oil emulsion.

In a preferred embodiment of this invention, the active ingredient is a component of the rolling oil emulsion, preferably a cold rolling oil used to lubricate the rolls and article being handled during the cold rolling of steel. The active ingredient may also be a component of the rolling oil formulation such as for example surfactants, antioxidants, corrosion inhibitors, antiwear additives, rust preventatives, wetting agents, emulsifiers, lubricants, antifoams, and the like which may become depleted from the emulsion during use.

In a still further method of this invention, the measurement of step II(d) is utilized to activate the feed of the active ingredient to the rolling oil emulsion if the measurement shows a low level, and the feed of water to the rolling oil emulsion if the measurement shows too high a level of active ingredient being measured in the rolling oil emulsion.

Dyes used in the practice of this invention are chosen to have an absorption band in the visible spectrum, although dyes material absorbing in the non-visible area of the spectrum may also be utilized. It is particularly convenient for the absorption band to occur near a maximum output of a light emitting diode (LED), 555–780 nm. The dye must be soluble in the active ingredient to be measured, and must be stable in the rolling oil system to which the active ingredient is to be added. The concentration of the dye is proportional to the concentration of the active ingredient in the rolling oil emulsion since the ratio of dye to active ingredient is a known constant. By determining the dye concentration in the rolling oil emulsion, the amount of active ingredient present in the emulsion can be calculated.

Accordingly, the method of this invention is applicable to only those rolling oil systems, in which two or more phases of matter exist, and which systems are reflective, i.e.: applied light is reflected. This invention is particularly desirable for use with systems where turbidity will not allow measurement by other conventional light transmittance measurements. Examples of systems to which this invention is applicable accordingly include oil-in-water emulsions, water-in-oil emulsions, and aqueous and non-aqueous suspensions, dispersions of rolling oils, and the like. Examples of particular systems where this invention may find utility include methods for determining active ingredient concentrations in rolling oils, process fluids, tramp oil emulsions, and any other similar non-homogeneous system in which a dye can be added to an active ingredient in a direct concentration relationship.

The dye should as stated earlier, be soluble, or at a minimum evenly dispersed in the active ingredient to be measured since it is important that the dye be added in a constant, uniform, amount in direct proportion to the active ingredient. The actual amount of dye material will vary depending upon the reflectance of the system, the desirability, or non-desirability of imparting color to a system when a dye having a visible color is employed, the amount of active material present in the system, and, the signal to noise ratio of the particular detectors employed. Generally the dye may be added in as little as a few parts per million to as much as 1 percent by weight of the active material. Preferably, from 10 ppm–1000 ppm of dye is added based on the weight of the active ingredient to be measured. Most preferably, from 10 ppm to 500 ppm of dye is employed based on the weight of active ingredient added to the rolling oil emulsion which is to be measured.

The dye must absorb at a given wavelength to be useful in this invention. In a preferred embodiment of this invention, the dye will have a visible color, will be substantially inert to the active ingredient, and the remainder of the system into which the active ingredient will be added. The dye will absorb at a visible wavelength approximately complementary to its perceived color. While a dye having visible color is preferred, dyes having absorbing characteristics in the ultra-violet, or infra-red regions of the spectra may also be employed. When using a non-visible dye, a "complementary" wavelength is defined as a wavelength region for which the dye does not have an absorption peak.

Included among the commonly available visible commercial dyes that may be used in the practice of this invention are: chlorophenol red; p-nitrophenol; alzarin; bromothymol blue; brilliant yellow; cresol red; thymol blue; bromocresol green; oil red; oil blue; oil green; oil orange; Calcocid blue; Calcocid green; Rhodamine B; Rhodamine Ex; Automate Red B; Automate Blue S; Solvent Yellow 14; Solvent Blue 14; Solvent Red 26; Solvent Red 27; and Solvent Red 24. This list is by no means inclusive of the dyes that may be used, and as stated above, while visible dyes are preferable from an economic perspective, dyes have absorbency characteristics in the ultra-violet, or infra-red spectrum will also function within the scope of this invention. In selecting a particular dye, care should be taken to use a dye that will evenly disperse throughout at least one phase of the rolling oil emulsion. In an especially preferred mode, the dye selected will be soluble in the active ingredient to be measured.

DETAILED DESCRIPTION OF THE DRAWING

FIG. 1 shows a block diagram of an apparatus useful in practicing the process of the invention. In this Fig, numeral 2 generally refers to a red LED light source, and numeral 4 to a green LED light source. Light sources 2 and 4 are connected by fibre optic cable 8 to reference detector 6 which alternately reads the intensities of Green LED 4 and Red LED 2. LED light sources 2 and 4 are connected by fibre optic cables 12 and 14 respectively to probe 10. Probe 10 is adapted to allow the light from fibre optic cables 12 and 14 to be launched into rolling oil system 20 containing dye which has been selected to absorb light emitted for example by Green LED 4. Light reflected from rolling oil system 20 is reflected back through probe 10 and carried by fibre optic cable 22 to sample detector 30. Reference Detector 6 measures LED intensities from the sources themselves in order to compensate for source intensity variation with time. Sample detector 30 measures reflected light (alternately red and green) from system 20. A microprocessor, not shown, calculates the ratio of light reflected by the rolling oil emulsion at the peak wavelength (green) and the amount of light reflected by rolling oil emulsion at a nonabsorbing wavelength (red). The calculated ratio is then converted to a concentration by means of a previously determined calibration curve to be described herein. While described in terms of red and green LEDs, other visibly colored LEDs or other light sources not shown could be used, in conjunction with other dyes.

Reflectance spectroscopy is therefore particularly well suited for systems of this type. This type of spectroscopy is made practical in the practice of this invention by the use of a bifurcated fiber optic probe. The rolling oil is illuminated with light from one or more legs of the cable, preferably two legs, and reflected light is carried to a detector by the third leg of the cable. This configuration makes a convenient in-line probe that is suitable for monitoring the highly turbid emulsions.

As seen in the above discussion the dual light wavelength technique is employed. In this method, reference and sample beams are ratioed to eliminate sources of error common to both beams such as variations in turbidity or particle size. The reference beam is of a wavelength that is not absorbed by the dye or to any extent by the rolling oil system. The beam will then give compensation for changes in the nature of the reflecting matrix, in this case the emulsified rolling oil. The sample beam is of a wavelength that optimally is strongly absorbed by the dye and is also similarly influenced by the emulsion as the reference beam. Therefore by ratioing the intensity of the two beams, effects due to the matrix alone, such as turbidity and particle size, which would otherwise give false information as to the degree of dye absorption are eliminated.

Solid state LED light sources and filament sources as well have the undesirable property of intensity degradation with time. Over the term of a continuous analysis, the dye concentration would appear to change due to this effect. This effect can be eliminated by ratioing, for each light source, the light source intensity and reflected light intensity from the emulsion as is practiced in this invention to be explained in detail below.

DETAILED DESCRIPTION OF THE INVENTION

In the practice of the invention, red dye is added to a rolling oil at a level of from 10 to 500 ppm based on the weight of the active ingredient. An emulsion is then prepared from the rolling oil, usually containing about 3 percent by weight rolling oil containing dye, and 97 percent by weight water. The dye utilized has a peak absorbance at 515 nm and is broad enough to overlap with the output of a green LED at 555 nm±40 nm. A red LED giving an output of 660 nm±40 nm is used as a reference since the dye shows no absorption in that wavelength range.

In order to make all the necessary corrections discussed above, four-optical intensity readings are made. The process is described as follows Referring to FIG. 1, reference detector 6 measures the intensity from the green source itself, $\text{Ref}_{green}$.

Reference detector 6 measures the intensity from the red source itself $\text{Ref}_{red}$.

Sample detector 30 measures the intensity of the green source reflected from the emulsion via probe 10, $\text{Sam}_{green}$.

Sample detector 30 measures the intensity of the red source reflected from the emulsion via probe 10, $\text{Sam}_{red}$.

By taking the ratios, $\text{Ref}_{green}/\text{Sam}_{green}$ and $\text{Ref}_{red}/\text{Sam}_{red}$, the reflected intensities for the green and red light sources are corrected for light source variations and temperature effect. The corrected reflectance ratios are referred to herein as $\text{Ratio}_{green}$ and $\text{Ratio}_{red}$, respectively.

Dye absorbance is defined as the log of the ratio of the corrected reflected light intensities, Dye absorbance=log $[\text{Ratio}_{red}/\text{Ratio}_{green}]$.

Oil concentration (O) is defined in equation I below:

$$O = k(\text{dye absorbance}) + c \qquad \text{(Equation I)}$$

where k is a slope constant determined during calibration and c is an offset term determined during calibration.

The above procedure is performed on a number of rolling oil emulsion samples. At least two samples of different concentration must be used. A single calibration consisting of three points is described below:
Step 1: A rolling oil product is colored by the addition of 0.01–0.05% by weight dye, with properties noted above. A homogeneous colored (red) solution is obtained;
Step 2: 1.0% emulsion is prepared by mixing together 1 part of the colored rolling oil with 99 parts water. A colored, turbid emulsion is obtained.
Step 3: A dye absorbance value is determined using the above procedure;
Step 4. A 2.0% by weight emulsion is prepared and another dye absorbance value is found;
Step 5. A 3.0% emulsion is prepared and a dye absorbance value is found;
Step 6. The k and c values in Equation I, above are determined by standard algebraic methods in which k is the least squares slope of the line through the three points and c is the y-intercept of the typical graph.

From the now known constants, k and c, the measurement procedure performed on unknown compositions of rolling oil emulsions prepared from the dye-containing oil product will yield the concentrations of the rolling oil in the emulsion.

In another mode of practicing this invention, a white light source (tungsten lamp) and two monochromatic detectors are employed. This mode allows for a simplified hardware design, especially for the fiber optic cable. Only a simple bifurcated cable such as those available from Dolan-Jenner, of Woburn, Mass. need be utilized.

This design may be further simplified in that only two reflectance readings are required compared to four optical readings for the mode of this invention which utilizes two monochromatic light sources. This is the result of the fact that the same light source is utilized to generate both wavelengths, one that is strongly absorbed by the dye, and another that is not absorbed by the dye. As will be seen by those skilled in the art, the device in this "mode" fits well within the scope of FIG. 1, with the LEDs being replaced by the tungsten light source and the elimination of fiber cable legs 8 and reference detector 6. Referring to FIG. 1, and describing FIG. 1 for a tungsten light source mode, tungsten lamp 2 is coupled to one smaller leg 12 of fiber optic cable to project white light into emulsion by the probe end 10 of the cable. Reflected light from the emulsion is transmitted from probe end 10 through cable end 22 to a photodiode assembly 30 described below. Two photodiode readings are taken, $\text{Sam}_{green}$ and $\text{Sam}_{red}$.

Dye absorbance is calculated in a similar manner as for the LED mode, dye absorbance=log $[\text{Sam}_{red}/\text{Sam}_{green}]$. Source intensity variations and changes in the reflecting emulsion matrix are automatically compensated by ratioing the two intensity readings. The photodiode assembly 30 may be conveniently made by machining black delrin plastic. It consists of two mating cylinders that are screwed tightly together to couple the light from the end of the optic cable into the two filtered photodiodes simultaneously and equally. A filtered photodiode is a photodiode having a specific wavelength filter such that it will respond only to a narrow wavelength range. In this mode, two filtered photodiodes are used, 520 nm±10 nm and 650 nm±10 nm. The cylinder holding the fiber optic cable may be hollowed out in a cone shape slightly larger than the cone of light emitted from the end of the cable (60° cone). The right side mating half has a similar cone into which the filtered photodiodes are positioned in holes.

The cone of light emitted from the end of the fiber optic cable 22 from the emulsion projects onto the filter ends of both photodiodes. Each photodiode output is read separately by the A/D converter using a multiplexer (MUX). Operation of the instrument is otherwise identical to that when two separate light sources are employed.

Equipment useful in the practice of this invention is available from commercial sources. The analyzer shown in FIG. 1 consists of two sections, a digital board, and an analog board electrically connected together. The microprocessor system in the digital section controls the operation of the instrument, calculates dye concentration, and communicates with the user. The analog board contains components to generate useable voltages from the detectors.

For the first mode, the digital board employed was purchased from Iota Systems, Inc., Incline Village, Nev. It contained the basic microprocessor circuitry. It contained 32K random access memory (RAM), and 16K erasable programmable read only memory (EPROM). The source LEDs 2 and 4 and detectors were mounted on a small prototyping area to which the smaller legs of the bifurcated fiber optic cable were coupled. By means of metal oxide semiconductor field effect transistor (MOSFET) switches, the microprocessor turned the LEDs on and off at proper times in sequence with a multiplexer that routed the appropriate detector signals to the analog to digital (A/D) converter. With 12-bit resolution, the A/D converter transformed the detector voltages into digital representations that were used by the microprocessor to calculate absorbence according to Equation I above. The dye concentration was shown on a digital display and transmitted to a host computer via RS232 communications. A power supply provided 5V DC which was required by the analyzer.

Another component of the subject analyzer was configured to contain a liquid crystal (LC) display, user input keys, connectors for the LEDs and detectors.

Photodiode current, generated when light falls onto a detector's active surface, is converted to a voltage by a field effect transistor (FET) operational amplifier. It is configured as a current to voltage(I/V) converter combined with a two pole low pass frequency filter ($f_c$=1000 Hz) to reduce noise.

The detector voltage is further amplified with a variable gain adjustment. The user could thus set gain manually so that the detector voltage is properly scaled to span the full range of the A/D converter (0–10V). For additional adjustment flexibility, potentiometers were installed to control the LED currents, which also affect the final detector outputs. Circuitry for both detectors is nearly identical. A multiplexer is used to route the desired detector signal to the A/D converter for further processing. The multiplexer is controlled by an I/O line from the microprocessor. The output signal from the multiplexer is buffered and filtered before being sent to the A/D converter.

The fiber optic probes useful in this invention are now available from a variety of commercial sources. A useful probe can be fabricated from a bundle of 12,500 glass fibers 2 mils in diameter and 1 meter in length. The common end was epoxied into a solid cylinder 3 inches long and 0.25 inches in diameter. The end was sheathed in PVC heat shrink tubing, cut and polished for good light transmittance. This is the portion of the cable that was immersed into the non-homogeneous emulsion. This portion is the probe (10). The immersed cable end may be capped with clear acrylic to prevent damage from exposure to the hot emulsion.

The remaining part of the bundle was divided into three strands: two of approximately 0.1 inch in diameter and a third of approximately 0.2 inch in diameter. The largest leg is used to send reflected light from the emulsion to the sample detector. It was mounted in a brass tube with epoxy and polished. The photodiode was epoxied into a Swagelok connector that accepted the cable end. A shielded electrical cable was also embedded in the connector for the detector output. Whether the probe is purchased or made is of no consequence to the spirit and intent of this invention.

The two other legs of the cable are used to transmit the LED light beams to the emulsion. Each leg and a separate 0.5 mm plastic fiber, 8, were mounted in a plastic fitting and connected to an LED source. The other ends of the fibers were also mounted in a fitting and were connected to detector 6, and were utilized for source intensity drift correction. The cables themselves were wrapped in polyvinyl chloride (PVC) shrink-wrap.

When an LED is energized, both detectors are simultaneously illuminated. The fiber carries the source light to the reference detector, and the sample detector receives light reflected back from the emulsion. The multiplexer is used to read each detector output signal.

To prevent ambient light errors, dark readings are taken during each measurement cycle. In this mode, both LEDs are off and detector readings are made. If voltages higher than a previously defined value are discovered, it is indicative of an equipment problem.

In operation the analyzer asks the operator to immerse the probe into the sample or to check its integrity if it is already installed in a flow through connector. One by one, each of the four detector signals are sampled and the voltages displayed. At each one the operator can adjust the appropriate potentiometer to make sure the signal is in the proper range.

In the analysis mode, the four detector values are obtained for each cycle. A single detector value is an average of 20 A/D conversions. In the calculation of dye concentration, 24 cycles are performed and the results averaged in a period of about 30 seconds. Once per cycle dark measurements are made. The four numbers are put into Equation I to give an absorbence value which is displayed.

In the testing described below, the probe was mounted in a tee fitting with a rolling emulsion circulating through it by means of a peristaltic pump. A glass beaker holding 250 ml of emulsion was kept hot for the measurements because the rolling oil formulation contained grease which came out of solution at lower temperatures.

The method of the invention was followed using the apparatus substantially as described above.

Table I shows the average results of 20 readings from five independent tests of Nalco® 6128, a commercially available rolling oil, at 2% oil concentration. The neat oil contains 250 ppm of Solvent Dye 24 (Keyplast Red A) from Keystone Aniline. The concentration varies ±0.1% from the actual oil level of 2.0%.

Table II shows the filtration results of a 1.3% oil emulsion of Nalco 6128 through a 1.0$\mu$ SS filter. This test was done because the rolling oil emulsions used in the plant contain debris such as metal fines and other particulate from the rolling operation which would interfere with the analysis. Particle size was measured also using a Coulter® TA II particle analyzer because fine-pore filters can exert shearing forces on the emulsion particles and possibly could have caused deviation in the analyzed concentration.

TABLE I

REPEATABILITY OF ANALYZER READING
VERSUS EMULSION CONCENTRATION
(2.0% NALCO -6128)

| Test Number | % Concentration (Average value of 20 readings) |
|---|---|
| 1 | +2.0 |
| 2 | +1.9 |
| 3 | +2.2 |
| 4 | +2.1 |
| 5 | +1.9 |

TABLE II

EFFECT OF FILTRATION ON ANALYZER READING
(1.0μ Stainless Steel Cartridge Filter; 1.3% Nalco 6128)

| Time (min.) | % Concentration | Coulter Counter Mean (50%) Particle Size (μ) |
|---|---|---|
| 10 | +1.3 | 15.2 |
| 20 | +1.1 | 14.0 |
| 30 | +1.2 | 14.0 |

Table III evaluates pH and pump shearing effects on the rolling oil emulsion. The pH of the emulsion will cause a variation in particle size as would the shearing effect of the centrifugal pump. As in Table II, deviations could occur as the conditions of the system change.

Table IV shows a crosscheck of the oil concentration by analysis versus the actual oil level used to make up the emulsion. Included are the Nalco 6128 controls (i.e. rolling oils without dye) at three different concentrations to verify that oil concentration without dye did not play a role in the analytical results. Three different levels of oil containing the dye were then prepared and analyzed to determine the accuracy of the method at different oil levels.

TABLE III

EFFECT OF RECIRCULATING PUMP SHEAR ON ANALYZER READING
1.3% 6128 Emulsion

| | pH = 5.5 | | pH = 6.4 | |
|---|---|---|---|---|
| Time (min.) | % Concentration (Avg. of 20 readings) | Coulter Counter 50% Value (μ) | % Contration (Avg. of 20 readings) | Coulter 50% Value (μ) |
| 10 | +1.4 | 21.5 | +1.4 | 20.3 |
| 20 | +1.3 | 19.0 | +1.3 | 15 |
| 30 | +1.2 | 18.5 | +1.3 | 14 |
| 40 | +1.2 | 18.9 | +1.4 | 14 |
| 50 | +1.2 | 18.2 | — | — |
| 60 | +1.2 | 18.7 | — | — |

TABLE IV

CROSSCHECK OF OIL CONCENTRATION BY ANALYSIS VERSUS ACTUAL OIL LEVEL

| Actual oil Concentration | Product Concentration by Analysis (%) |
|---|---|
| Control (1.0%) | −0.1 |
| Control (3.0%) | +0.1 |
| Control (3.5%) | 0.0 |
| 1.0% 6128 with dye | +1.1 |
| 3.0% with dye | +3.0 |
| 3.5% Nalco 6128 | +3.6 |

As seen from the above examples, the analysis method of this invention accurately provides concentration information on additives contained in non-homogeneous systems.

Having thus described our invention, we claim:

1. A method for determining the concentration of an active ingredient contained in a rolling oil emulsion having two or more distinct phases at least one of said phases being liquid which comprises:
   a) preparing a calibration curve through the steps of:
      i) adding to the active ingredient contained in the rolling oil emulsion a known amount of a light absorbing dye having a known peak absorbance wavelength within the range from about 515 nm to about 595 nm, said dye being capable of being homogeneously dispersed throughout at least one phase of the rolling oil emulsion;
      ii) adding the active ingredient containing the known amount of light absorbing dye material to the rolling oil emulsion;
      iii) applying a light source to at least a portion of the rolling oil emulsion containing the active ingredient;
      iv) measuring the amount of light reflected from said emulsion at the peak absorbing wavelength of the dye to obtain a first reflectance value and measuring the amount of light reflected from said emulsion at a wavelength other than the peak absorbing wavelength of the dye within the range from about 620 nm to about 700 nm to obtain a second reflectance value for at least two different concentrations of the active ingredient in the rolling oil emulsion;
      v) ratioing the second reflectance value to the first reflectance value for each concentration of active material and establishing a calibration curve; and then,
   b) determining the concentration of active ingredient in a rolling oil emulsion during use through the following steps:
      i) obtaining a sample of emulsion after the emulsion has been in use;
      ii) measuring the amount of light reflected from said emulsion sample at the peak absorbing wavelength of the dye to obtain a first reflectance value and measuring the amount of light reflected from said emulsion at a wavelength other than the peak absorbing wavelength to obtain a second reflectance value;
      iii) ratioing the second reflectance value to the first reflectance value and comparing the ratio to the calibration curve of step a(v); and then,
      iv) determining the concentration of the active ingredient in the rolling oil emulsion.

2. The method of claim 1 wherein the rolling oil emulsion is composed of two immiscible liquid phases.

3. The method of claim 1 wherein the difference between the wavelength of the peak reflectance for the dye and the wavelength for the non-peak reflectance is at least 10 nanometers.

4. The method of claim 1 wherein the dye absorbs in the visible light range.

5. The method of claim 1 wherein the dye absorbs in the visible light range, the non-peak wavelength is a complementary visible color to the dye, and the dye is soluble in the rolling oil.

6. The method of claim 1 wherein the reflectance measurements are made by the use of a fibre optic probe which is disposed within the rolling oil emulsion, and the output of such fibre optic probe is split into two channels, one of which is used to measure reflectance of the dye at the peak wavelength, and the other of which is used to measure reflectance of the dye at the non-peak wavelength.

7. A method for determining the concentration of a rolling oil contained in a rolling oil emulsion which comprises:
   a) adding to the rolling oil a known amount of a light absorbing dye, wherein the peak wavelength of the light absorbed by said dye is known;
   b) forming a rolling oil emulsion containing a known amount of the rolling oil;
   c) applying a light source to at least a portion of the rolling oil emulsion containing the rolling oil;
   d) measuring the amount of light reflected from said emulsion at the peak absorbing wavelength within the range from about 515 nm to about 595 nm to obtain a first reflectance value and measuring the amount of light reflected from said emulsion at a wavelength other than the peak absorbing wavelength within the range from about 620 nm to about 700 nm to obtain a second reflectance value for at least two different concentrations of the rolling oil in the rolling oil emulsion;
   e) ratioing the second reflectance value to the first reflectance value for each concentration of rolling oil and establishing a calibration curve;
   f) obtaining a sample of rolling oil emulsion in which the quantity of rolling oil is unknown;
   g) measuring the amount of light reflected from said emulsion sample at the peak absorbing wavelength of the dye to obtain a first reflectance value and measuring the amount of light reflected from said emulsion at a wavelength other than the peak absorbing wavelength to obtain a second reflectance value;
   h. ratioing the second reflectance value with the first reflectance value and comparing the value obtained with the calibration curve of step e; and then,
   i. determining the concentration of the active ingredient in the rolling oil emulsion.

8. The method of claim 7 wherein the dye material absorbs in the visible light range.

9. The method of claim 7 wherein the difference between the wavelength of the peak reflectance of the dye and the wavelength for the non-peak reflectance of the dye is at least 10 nanometers.

* * * * *